(12) United States Patent
Molander et al.

(10) Patent No.: US 11,253,664 B2
(45) Date of Patent: Feb. 22, 2022

(54) EMERGENCY RESPIRATORY VENTILATOR

(71) Applicant: VENTI-NOW, Montgomery, OH (US)

(72) Inventors: John Carroll Molander, Montgomery, OH (US); Howard Jay Kalnitz, Mancos, CO (US); Arthur Joseph Koehler, Liberty Township, OH (US); Michael Gary Nease, Hamilton, OH (US)

(73) Assignee: VENTI-NOW, Montgomery, OH (US)

(*) Notice: Subject to any disclaimer, the term of this patent is extended or adjusted under 35 U.S.C. 154(b) by 0 days.

(21) Appl. No.: 17/234,647

(22) Filed: Apr. 19, 2021

(65) Prior Publication Data

US 2021/0322692 A1 Oct. 21, 2021

Related U.S. Application Data

(60) Provisional application No. 63/011,675, filed on Apr. 17, 2020.

(51) Int. Cl.
*A61M 16/00* (2006.01)
*A61M 16/20* (2006.01)
*A61M 16/08* (2006.01)
*A61M 16/10* (2006.01)

(52) U.S. Cl.
CPC .... *A61M 16/0072* (2013.01); *A61M 16/0084* (2014.02); *A61M 16/0833* (2014.02); *A61M 16/0875* (2013.01); *A61M 16/105* (2013.01); *A61M 16/208* (2013.01); *A61M 2202/0208* (2013.01); *A61M 2205/70* (2013.01); *A61M 2230/42* (2013.01)

(58) Field of Classification Search
CPC ............ A61M 16/0057; A61M 16/006; A61M 16/0072; A61M 16/0075; A61M 16/0078; A61M 16/0081; A61M 16/0084; A61M 16/0833; A61M 16/0875; A61M 16/105; A61M 16/207; A61M 16/208; A61M 2205/70; F04N 49/12; F04N 49/1222; F04N 49/123; F04N 49/1256; F04N 49/1276; F04N 49/14; F04N 49/16; F04B 2201/0206; F04B 2203/10
See application file for complete search history.

(56) References Cited

U.S. PATENT DOCUMENTS

| | | | | |
|---|---|---|---|---|
| 3,973,564 A | * | 8/1976 | Carden | A61M 16/0045 128/205.14 |
| 4,207,884 A | * | 6/1980 | Isaacson | A61M 16/208 128/200.24 |
| 5,509,406 A | * | 4/1996 | Kock | A61M 16/104 128/200.24 |
| 6,155,257 A | * | 12/2000 | Lurie | A61H 31/005 128/204.18 |
| 10,912,903 B2 | * | 2/2021 | Fried | A61M 16/0051 |
| 2005/0284472 A1 | * | 12/2005 | Lin | A61M 16/0084 128/202.29 |
| 2009/0145437 A1 | * | 6/2009 | Halpern | A61M 16/0616 128/206.21 |

(Continued)

*Primary Examiner* — Colin W Stuart
*Assistant Examiner* — Douglas Y Sul
(74) *Attorney, Agent, or Firm* — James Pingor

(57) ABSTRACT

An emergency respirator ventilator that comprising an air cylinder and piston/piston rod for compressing an air bag to transmit air to a patient, e.g., during situations where fully equipped ventilators are not immediately available.

15 Claims, 9 Drawing Sheets

(56) References Cited

U.S. PATENT DOCUMENTS

| | | | |
|---|---|---|---|
| 2012/0145151 A1* | 6/2012 | Bergman | A61M 16/0078 128/204.21 |
| 2017/0197047 A1* | 7/2017 | Minato | A61M 16/06 |
| 2019/0151602 A1* | 5/2019 | Tappehorn | F16K 15/148 |
| 2019/0232016 A1* | 8/2019 | Sayani | A61M 16/107 |
| 2020/0086075 A1* | 3/2020 | Mujeeb-U-Rahaman | A61M 16/0078 |
| 2021/0060274 A1* | 3/2021 | Lim | A61M 16/022 |

* cited by examiner

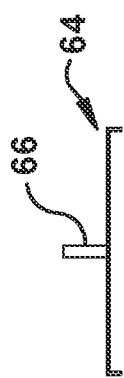
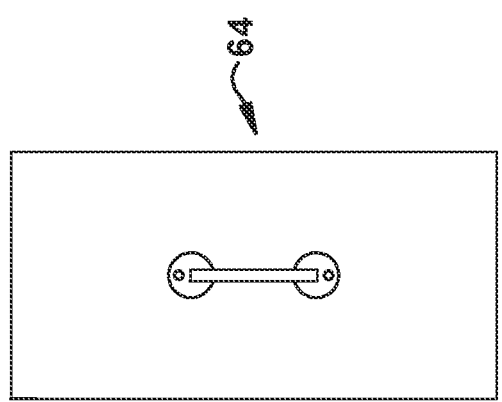
Fig. 6B
Fig. 6A
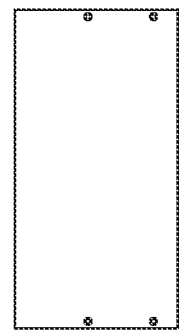
Fig. 5D
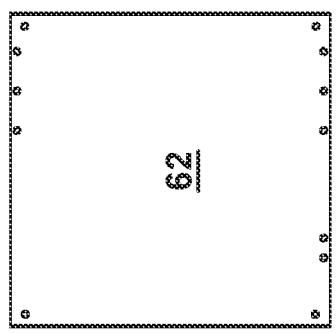
Fig. 5A
Fig. 5C
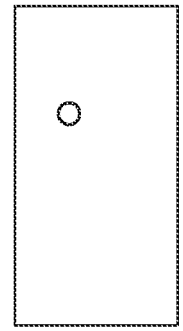
Fig. 5B

EMERGENCY RESPIRATORY VENTILATOR

CROSS-REFERENCE TO RELATED APPLICATION

This claims the benefit of U.S. Provisional Application No. 63/011,675 entitled "EMERGENCY RESPIRATORY VENTILATOR" filed on Apr. 17, 2020, which is incorporated herein by reference in its entirety.

FIELD OF THE INVENTION

This innovation relates to respiratory ventilators, and in particular to ventilators and breathing apparatus for use in emergency situations.

BACKGROUND

In emergency situations wherein civilian/human respiratory failure occurs due, for example, to a pandemic, a widespread danger to public health is presented. Hospital equipment is often fully exhausted with respect to respiratory problems, particularly with respect to ventilators. A requirement in emergency situations for inexpensive yet effective ventilators requires that they be easily manufactured, lightweight, easily transportable and be able to be used to keep a patient alive for a period of time (e.g., number of hours/days) without the need for expensive, medical grade oxygen to power the ventilator. There have been a number of patent and patent applications directed to this type of respiratory device. U.S. Pat. No. 8,534,282 (the "'282 patent") discloses a device for automatically squeezing and releasing an air-mask-bag-unit (AMBU) bag, also referred to as a bag-valve-mask (BVM). More specifically, the '282 patent discloses a flexible self-inflating resuscitator squeeze bag with an intake tube at one end and an outlet tube at the other end. There are a number of extra additions. These include a volume controller of the air/gas intake, an operator adjustable squeezing assembly, an adjustable cycle controller, warning indicators for too low a pressure, and a low battery indicator that is used to power a controller/microprocessor. The latter is used to control cycle frequency and squeezing volume, automate and/or self-adjust the amount of squeezing pressure and/or volume to accommodate various physiologies of patients. Although the '282 patent discloses an interesting device, it is quite complicated and would be rather expensive and, therefore, not adequate to meet the need in emergency management scenarios. The '282 patent discloses both a one-time use with a disposable product, as well as ones that are much more complicated. The '282 patent discloses a squeeze bag that is dropped into a holder in a slot. The flexible resuscitator squeeze bag is a flexible self-inflating product that does not require the attachment of an intake tube from the bag. The '282 patent discloses a fairly complicated electronic circuitry for accomplishing a wide variety of useful outputs, but this necessarily requires excessive expense for preparing an emergency unit.

Another patent is U.S. Pat. No. 8,714,156 (the "'156 patent") which provides a ventilator system for respiratory distress due to the onset of an epidemic or pandemic disease state. This device, although apparently having useful features, is also rather involved and includes a rather complicated electronic circuit, thus making the unit difficult and time consuming to manufacture. In addition to the excessive time of manufacture, these different aspects render the product made by the '156 patent too expensive for emergency use. The '156 patent describes two embodiments. In one embodiment, there is a flow control valve operable to control the flow of gas from an inhalation conduit to an air entrainment area that is connected to two conduits. One leads to a port for receiving atmospheric air, and another to a gas shut off mechanism that senses a pressure state in the inhalation conduit and controls a valve to prevent air from passing out of the port and into the atmosphere. In the other embodiment, a patient flow control valve operably connected to a control gas reservoir, a patient control valve operably connected to control gas input from the reservoir via an inhalation conduit, a patient interface separated from the inhalation conduit by the flow control input valve, a shut-off mechanism that senses a pressure state in the inhalation conduit, where the ventilator is capable of responding to varying patient needs via at least one control. Another embodiment includes a gas shut-off mechanism that senses a pressure state in the inhalation conduit, and the ventilator also has means for controlling at least one of peak inspiratory pressure (PIP), and positive end expiratory pressure (PEEP), the level of oxygenation and respiration rate.

BRIEF SUMMARY

The subject innovation provides an emergency respirator ventilator that can mechanically ventilate a respiratory care patient.

In one aspect, the innovation replaces/assists manual squeezing of a self-inflating bag with an adjustable rate and stroke piston that provides Volume Control (VC) ventilation, where a clinician determined tidal volume is delivered each breath cycle.

Yet another aspect of the innovation provides the foregoing type of ventilator which can be prepared with stock (e.g., off-the-shelf) parts and medical grade materials.

It is still another aspect of the innovation provides for a pneumatic unit (e.g., an electro-pneumatic unit) that includes relatively few moving parts.

Yet still another aspect provides an emergency respirator ventilator that can use existing medical compressed air where supplied in clinical locations.

Another aspect provides an emergency respirator ventilator which is small in dimensions and lightweight, rendering it readily portable.

A still further aspect of the subject innovation provides an emergency respirator ventilator which can be produced in large numbers (e.g., around 5,000 units per week).

Another aspect of the innovation is that it be "a universal unit" in that it can accept BVM ventilation bags from a variety of producers and a variety of sizes, such as for use with both adults and children.

According to an aspect, an embodiment of the innovation provides a one-way flutter valve in the patient breathing circuit configured to accommodate a range of different BVM exhaust systems from a variety of BVM producers. The one-way flutter valve prevents the exhalation of a patient from going back up the tube in the wrong direction.

An additional aspect of the innovation is the ability to adjust the tidal volume of air to the lungs by changing the stroke length of the piston (in this respect, the range of air to the lungs for adults is typically 300-700 mL, but other ranges may be desirable.)

Yet a still further aspect of the innovation is the ability to adjust the inhalation and exhalation (I/E ratio) time of the breathing cycle by adjusting the piston speed (the Respiration Rate is the inverse of sum of the inhalation and exhalation time and is shown as breaths per minute (bpm).

A still further aspect of the innovation is that it is safe to use without requiring a series of complicated readouts and the like which may not be necessary for emergency situations.

It is yet an additional aspect of the present innovation is the provision of a device for the independent adjustment of the I/E ratio and the Respiration Rate (bpm) to allow the medical staff to tune the unit to the patient breathing cycle and avoid ventilator dyssynchrony.

It is also another aspect of the present innovation to provide a sensor that triggers an alarm if the pressure is too low/lost (e.g., due to a BVM bag break or a hose disconnect in the inhalation breathing circuit) or if pressure is too high (e.g., due to blockage or patient lung changes).

A yet further aspect of the present innovation is the respirator ventilator according to the innovation can be provided with a display that reads I/E ratio, Inspiration Time, Respiration Rate, PEEP, and Peak Inspiration Pressure.

It is also an aspect of the present innovation is the respirator ventilator can be compatible with PEEP valves in a patient exhaust breathing circuit with the addition of commercial one-way valve in the inhalation breathing circuit.

In another aspect, an embodiment of the innovation may provide a dome shaped compression plate for controlling the location of the BVM bag in the compression chamber so that it does not rise up in the chamber but rather is urged into a receiving surface in the lower opposing side of the compression chamber.

A related aspect of the present innovation is the provision of an elastomeric material such as silicone rubber bands mounted on the back wall of the chamber holding the air bag to minimise bag movement.

A further aspect of the innovation to prevent dyssynchrony is the provision of patient triggered breathing in an Assist Control (AC) machine ventilation mode. This mode may be set by the clinician/technician on the control panel. In AC mode the ventilator delivers a fully supported breath whether time or patient triggered.

A still further aspect of the innovation provides controls for adjusting the trigger pressure. When the patient draws a spontaneous breath that lowers the pressure in the expiration tube below the PEEP level by a pre-set value, the ventilator responds by delivering a fully supported breath of the prescribed tidal volume. This pre-set value is known as the trigger sensitivity. It may be adjusted by the clinician/technician (e.g., by a knob on the control panel).

Another aspect of innovation is the inclusion of an uninterrupted power supply (battery backup) to ensure alarms and functions continue if line power is interrupted.

Another aspect of the innovation is the inclusion of a flow sensor to which the patient breathing circuit attaches. This allows for the monitoring of airflow to the patient and integration of the tidal volume of air delivered.

Overall, a general advantage of the innovation is that it provides an emergency respirator ventilator which is effective in use, efficient in operation and economical to produce and supply as required.

BRIEF DESCRIPTION OF THE DRAWINGS

FIGS. 5 and 6 are schematic views of a support frame and a cover as further components of an embodiment of the innovation.

DETAILED DESCRIPTION

Figure 1:
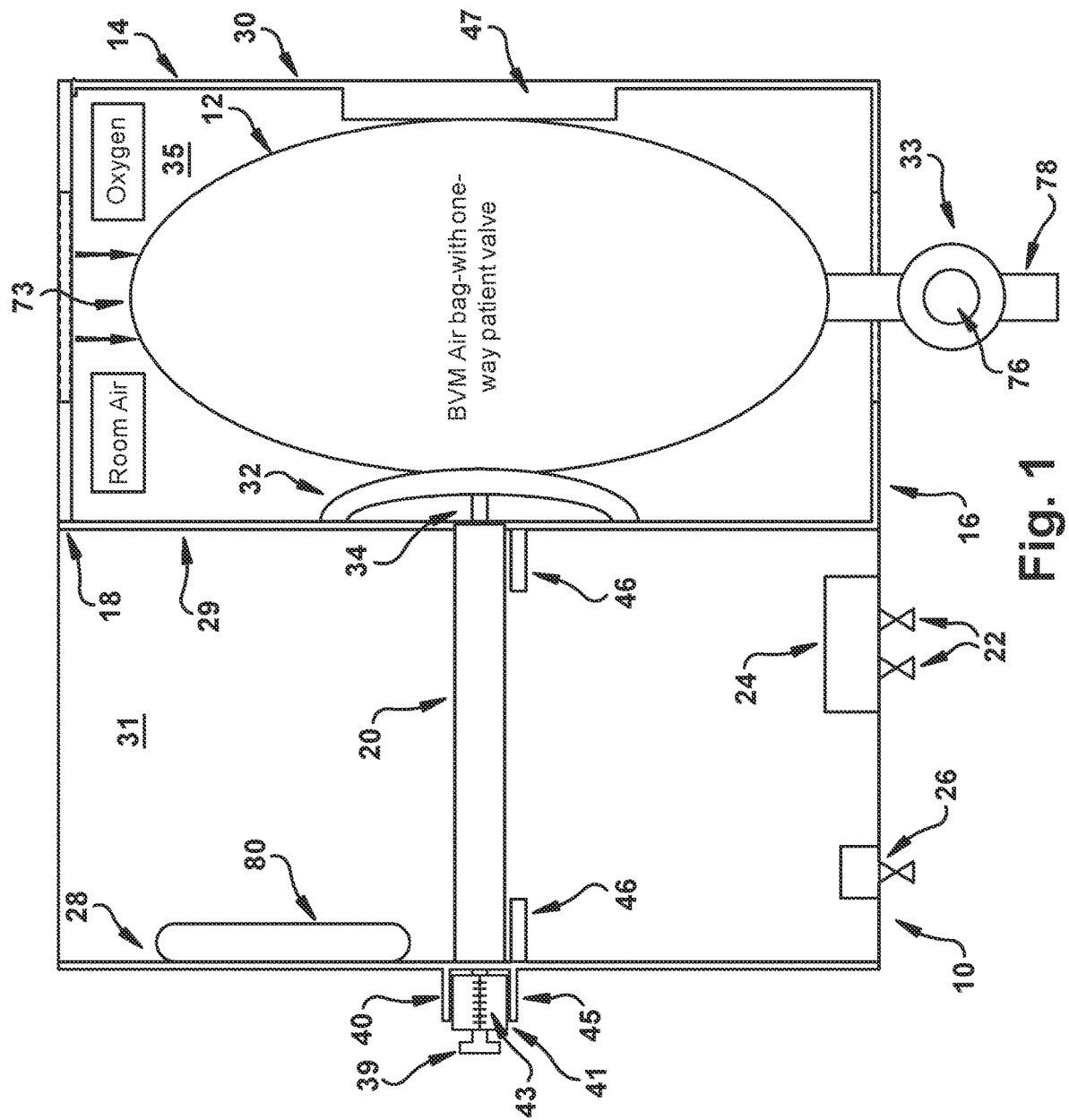
FIG. 1 is a schematic plan view of a respirator ventilator according to an embodiment of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details.

While, for purposes of simplicity of explanation, the one or more methodologies shown herein are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events. Moreover, not all illustrated acts may be required to implement a methodology in accordance with the innovation.

Currently, some of the products described below are made by Bimba Manufacturing Co., located at University Park, Ill. Bimba is part of IMI Precision Engineering, which is a leader in motion and fluid control technologies. Many of the parts described below refer to different off-the-shelf products, whose exact characteristics can be found in publicly available catalogues and from online sources. It is to be appreciated that the below-described products are examples of components that can be used and that one of skill in the art may determine a product from a different manufacturer/producer will provide the same or substantially the same function.

As described herein, the innovation provides for a product which can be prepared inexpensively using a respiratory system which is both effective and efficient is use. In some embodiments, the device may include a respiration bag kit or bag valve mask (BVM) that may be most any size. Furthermore, the device can include an alarm to report the breakage (or failure) of a bag or an indication that a hose has come off, is loose, or otherwise dislodged. In one embodiment, the innovation can further employ use of an exhalation HEPA filter (the HEPA filter is a highly efficient, small micron particulate air filter that enables it to trap viral matter and minute bodies). In another embodiment, a PEEP (positive end-expiratory pressure) valve may be included. A PEEP valve is used, for example, where the patient is sedated and back pressure is needed to keep the lungs of the patient from collapsing. In one embodiment, the unit may be powered by compressed air for the pneumatics, with low voltage electric power used to power alarms. By design, the unit is small, lightweight and can be sold for a reasonable price. The disposable BVM respiration kits are believed to be around $20.00 (in 2020) rendering it simple and inexpensive and able to meet emergency situations.

In one aspect, the innovation provides a respirator ventilator. As described below, a respirator ventilator according to an embodiment may comprise a pair of adjacent chambers. One chamber, referred to herein as the compressor chamber, is where an air bag is disposed. In an embodiment, the air bag is secured within the compressor chamber via at least one securing component. Suitable securing components include flexible bands (e.g., elastic bands); a receiving plate configured to accommodate the air bag, and the like. In one embodiment the air bag may secured by elastic bands. The air bag may be in a horizontal position having an air or oxygen intake port at one end and an oppositely located discharge end or discharge port. A tube device patient valve may be attached to the discharge end, through which air is discharged in response to the compression of the bag, and is transmitted to the patient through the discharge port. A second chamber, referred to herein as the cylinder chamber, houses a cylinder of a piston-cylinder assembly. In one embodiment, the piston-cylinder assembly is configured to drive a piston in a reciprocating motion through an orifice in a wall separating the compression chamber from the cylinder chamber. In one embodiment, there may be a top (e.g., a metal top) and side walls on the cylinder chamber to facilitate keeping the device clean in a medical environment. In addition, or alternatively, there may be a top wall. In one embodiment, the top wall may be a metal top wall. In one embodiment, the top wall of the compressor chamber may be clear or include an area through with the compressor chamber can be viewed to allow observation of the operation. One advantage of this configuration is that it makes it possible the use of air bags from many different suppliers, regardless of dimensional differences and exhaust port configurations. In one embodiment, the cylinder drives the piston towards the air bag to compress the air bag. The piston may be provided with a dome shaped piston head, referred to herein as a pressure plate, for compressing the air bag to force air out of the air bag through the tube device to the patient. The force of the pressure plate is applied above the middle of the air bag to maintain stability of the air bag by urging it against a receiving plate mounted on the opposing wall and to the lower corners of the compression chamber. This configuration may help to prevent erratic movement of the air bag towards the upper portion of the compression chamber.

According to an embodiment, the cylinder-piston assembly may include a variable stroke piston having an adjustable effective length. In one embodiment, the effective length may be adjusted by means of a tube-within-a-tube device that operates according to a calibrated scale(s) on the inner tube. Likewise, the rate of the reciprocating movement of the piston can also be varied to control the Respiration Rate and I/E ratio. These controls enable the adjustment of the minute volume of air being transmitted to the patient where Minute Volume is the product of Tidal Volume and Respiration Rate.

In one embodiment, the respirator ventilator may be compatible with PEEP valves by means of a one way flapper valve in an inhalation breathing circuit. Breathing circuits of the nature needed for a respirator ventilator are readily available from FDA approved medical suppliers. A single limb breathing circuits of this nature are typically supplied with flexible corrugated inhalation and exhalation tubes, a patient wye or adaptor, pressure monitoring tube and an exhalation valve (e.g., CareFusion 55-001795 by Vyaire Medical). This flapper valve prevents the exhaust air from bypassing the PEEP valve. Thus, for example a pressure sensor alarm module is connected by flexible tubing to a patient wye connector pressure port, and a tee connector, (e.g., an AirLife connector (004081))—the discharge from the latter to a one-way disposable flapper valve. An example of a suitable flapper valve includes an AirLife one-way valve (001800). In one embodiment, the discharge from the latter valve leads both to the mask or intubation tube to the patient, and the exhaust air valve to a HEPA filter and PEEP valve and then to an exhaust to the room environment.

In one embodiment, the respirator ventilator may include a display for one or more functions to provide information to a medical provider and/or caretaker. For example, the display may be Respiration Rate, I/E ratio, PEEP, Inspiration Time, PIP, an air flow display and/or a tidal volume display.

In one embodiment the device includes a single limb patient circuit with an exhalation valve (e.g., CareFusion 55-001795 by Vyaire Medical). The pressure to supply this exhalation valve comes from tubing connected to a Tee placed in the patient circuit immediately downstream from the BVM. As the bag is squeezed the inhalation circuit is pressurized and the resulting pressure closes the exhalation valve ensuring delivery of the set tidal volume to the patient. When the pressure drops at the end of the BVM compression stroke the exhalation valve opens allowing the lungs to expire air through the PEEP valve and filter into the room atmosphere. This simple pneumatic piping eliminates the need for complex pumps and electric valves to control the patient exhalation valve.

According to an aspect, the respirator ventilator may be pneumatically powered/controlled, electrically powered/controlled, or both. As described above, the piston assembly may be pneumatically controlled. In one embodiment, the piston assembly may be controlled electrically, either as a back-up in case of failure of the pneumatic control or solely electrically-controlled. In one embodiment, other features of the respirator ventilator may be electrically controlled (e.g., the display(s) and alarm(s) while the piston assembly is pneumatically controlled. In one embodiment, a battery may provide energy to the unit.

Turning now to FIG. 1, FIG. 1 shows in schematic form a respirator ventilator 10 according to an embodiment of the innovation. Respirator ventilator 10 incorporates a self-inflating air bag 12 that is disposable. Self-inflating air bag 12 is incorporated in a housing 14. In the embodiment depicted in FIG. 1, housing 14 is shown as including three parallel walls. The walls may comprise sufficiently rigid material appropriate for medical device use. In one embodiment, the material may be a stainless steel plate (e.g., a 304 stainless steel plate). In the embodiment depicted in FIG. 1, the housing 14 has at its base a stainless BVM cradle plate 16 that has notches where the BVM bag is placed. In one embodiment, the dimensions of the cradle plate may have dimensions of 4" by 6". In one embodiment, plate 16 is a 1/16" 304 stainless plate. In one embodiment, the respirator ventilator 10 may include a receiving plate 47. The receiving plate 47 is configured to secure the BVM bag and facilitate compression of the BVM bag. The top of housing 14 is held in place by fasteners 18. In one embodiment, the fasteners 18 may be SS button head hex fasteners. Self-inflating air bag 12 is compressed by means of a cylinder. FIG. 1 further includes a front and rear mount double ended air cylinder 20. A suitable stroke double ended cylinder includes a double ended 3" stroke front and rear mount 9/16 bore cylinder (e.g., a Bimba 023DE-20). Operation of the front and rear mount double ended air cylinder 20 is controlled by two flow control valves 22 (e.g., Bimba FQPS2K). The latter controls a valve 24, such as a 4 way 5 port air pilot valve (e.g., Bimba M4A22006). Part of the control of the stroke double ended air cylinder 20 is controlled by means of a 3 port manual toggle (e.g., Bimba MV35), indicated by numerical indicator 26 in FIG. 1. It is to be understood and appreciated that while Bimba parts are described for use herein, other equivalent off-the-shelf parts can be employed without departing from the spirit and scope of this innovation and claims appended hereto. Further, it is to be understood and appreciated that the embodiments and aspects described herein are described using parts provided by specific manufacturers/distributors (e.g., Bimba). While these parts have been shown to be adequate for use, other equivalent or alternate off-the-shelf components can be employed and are to be included within the scope of this specification and claims appended hereto.

With continued reference to FIG. 1, air and oxygen are fed into one end of BVM bag 12 via inlet port 73 (see FIG. 9), and upon the compression applied to self-inflating (and disposable) BVM bag by pressure plate 32, air and oxygen are forced through a BVM one-way patient valve 33 to the patient. Domed pressure plate 32 is urged against BVM bag 12 by means of the linear motion of piston 38 (see FIG. 2) moving in front and rear mount double ended cylinder 20. Locking knob 39 is part of a "tube-in-tube" calibration device 45 (see FIG. 8) for adjusting the stroke of piston rod 34, on which a scale 43 is shown for making an exact setting.

Figure 2:
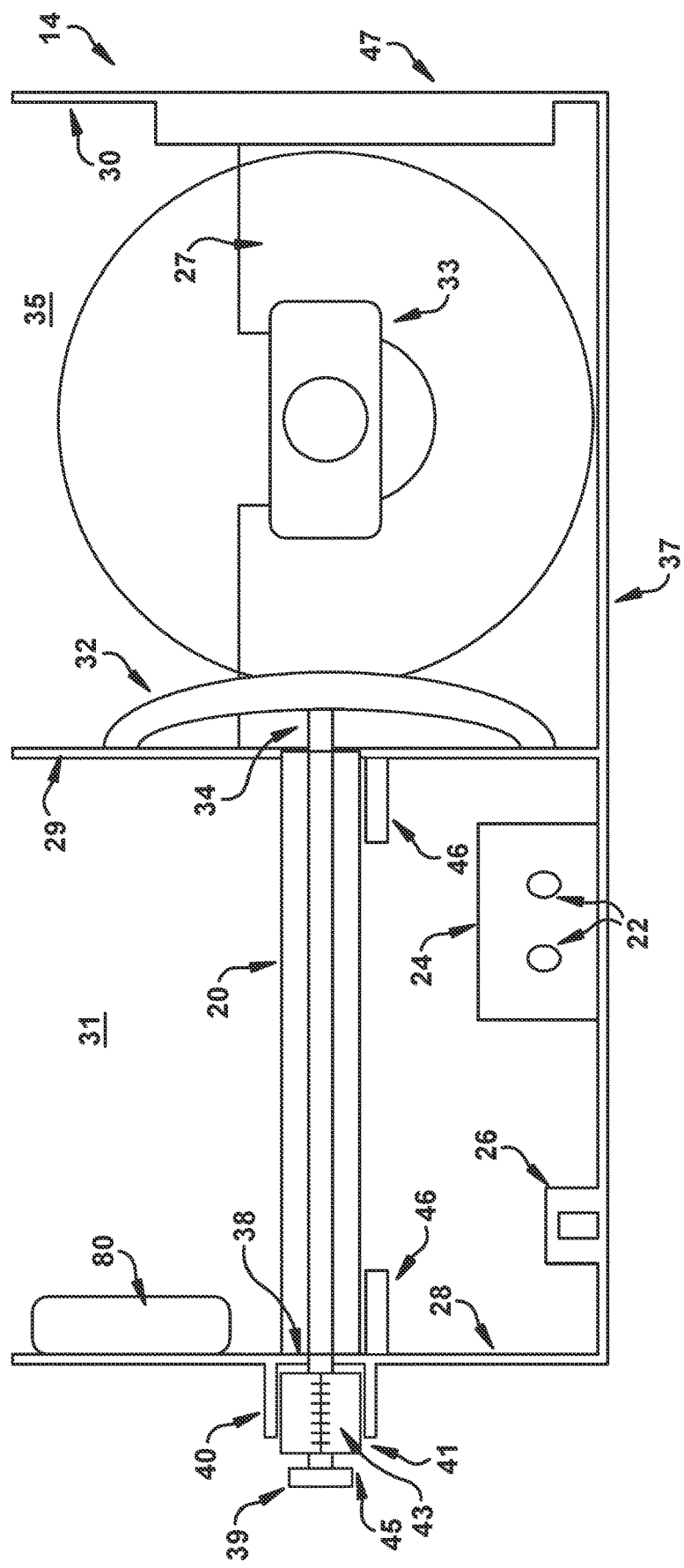
FIG. 2 is a side view of the respirator ventilator according to an embodiment of the innovation.

FIG. 2 is a side view of respirator ventilator 10 according to an embodiment of the innovation. FIG. 2 shows self-inflating air BVM bag 12 as being mounted on holding device 27. The front and rear mount double ended cylinder 20 is operationally attached to domed compression plate 32 which is moved in a reciprocal linear motion by means of a piston rod 34 extending an end of the front and rear mount double ended air cylinder 20, and a piston rod 38 extending to the other end of the front and rear mount double ended air cylinder 20. In one embodiment, the tidal air volume may be adjustable. Still referring to FIG. 2, the respirator ventilator 10 may include a locking knob 39 and threaded within adjustable graduated inner cylinder tube 41, as described above, and marked for tidal volume, and outer cylinder tube 40. (See FIG. 8.)

Continuing with FIG. 2, housing 14 includes three parallel plates forming two chambers. Plates 28 and 29 form a first chamber 31, and plates 29 and 30 form a second chamber or compression chamber 35. In one embodiment, plate 29 may comprise a stainless-steel plate (e.g., a 304 stainless steel plate). In one embodiment, plate 29 may have dimensions of 6" by 12". It is to be appreciated that the dimensions of plate 29 can be adjusted to accommodate different needs without deviating from the scope of the innovation. In one embodiment, stainless plates 28 and 30 may be each 1/16" thick, made of 304 stainless steel and have dimensions 4" by 6". The latter may be bent into a U-shape with a 12" base 37. Plate 29 may be a 12" by 6" plate that is 1/8" thick and holds front and rear mount double ended cylinder 20. Referring to FIG. 1, fasteners 18 (e.g., SS button head hex fasteners) are 1/16" SS button heads.

Still referring to FIG. 1, a four way five port pilot valve 24 is configured to change the direction of movement of piston rods 34 and 38 (see FIG. 2), and domed compression plate 32. In one embodiment, three port toggle switch 26 is an air on/off switch 26 that may be included. In an embodiment, the air on/off switch may be a three port manual detent toggle.

If needed in aspects, adapters may be provided to accommodate different sized tubing or piping (e.g., pneumatic pipe or flexible tubing. Suitable examples of adapters may include: two adaptors for 10-33 to 1/8 NPT (e.g., model D/855/A) and two PTC T-fittings such as two ports 1/4 and one port 5/32 (e.g., model C20630402-618).

In one embodiment, two stroke completion sensors 46 may be provided to reverse directions of the air cylinder. In an example, the sensors 46 can be Bimba model SCD-112. Alternatively, this can be accomplished through manual three-way pneumatic contact valves or electric switches that are depressed by the compression plate and tube-in-tube mechanism. There are alternatively a number of pneumatic switches, pressure switches, magnetic and proximity sensors that can detect the end of the set stroke. The electric switches can control an air solenoid to reverse the stroke.

Also provided are two flow controls 22 with an adjustment knob and locking nut. In one embodiment, Bimba model number FQPS2K may be used for controlling speed.

In one embodiment, a 1/8 NPT-1/4 OD tube straight may be provided as connectors (e.g., model number C24250218-618). A 1/8 NPT-5/32 OD tube straight as a connector may further be provided, (e.g., model number C2450418-618). Further included may be a 1/8 NPT-1/4 OD tube 90 degree as connectors, (e.g., model number C24470218-618). An 1/8 NPT-5/32 OD tube 90 degree as connectors may also be included, (e.g., model number C24470418-618). The final part of the tubing may include a 5/16" PE tubing, a 1/8" PE tubing and a compressed air inlet male bayonets fitting 1/4" NPT from various suppliers to adapt to dry medical compressed air supply. Hospitals use their own hoses for wall plates, and there are many different sizes used in hospitals in the United States.

Details of embodiments of the housing portion of respirator ventilator 10 according to an aspect of the innovation are shown in FIGS. 3-7, which depict an example according to an embodiment of the innovation. Referring first to FIG. 3A, a side plate 50 is shown. Side view of a side plate 50 indicates that side plate 50 may be formed as a rectangle with a U-shaped cut-out 52 formed therein to house a BVM bag. The U-shaped cut-out 52 helps put the BVM in position in the compressor chamber because the BVM should not be locked in the slot. In one embodiment, there may be two corner cut-outs 53 on the lower portion of side plate 50. U-shaped cut-out 52 is provided to form a resting place for holding device 27 shown in FIG. 2 of the BVM air bag 12. In an embodiment, a pair of elastic bands may be secured on eyebolts mounted on base plate 37. These bands may be configured to loop around the ends of the BVM and attach to open hooks on the top of the back wall. In one embodiment, a machined polyamide (e.g., Delrin®) receiving plate 47 is attached to the back wall to aid in holding the BVM during compression.

Figure 3B:
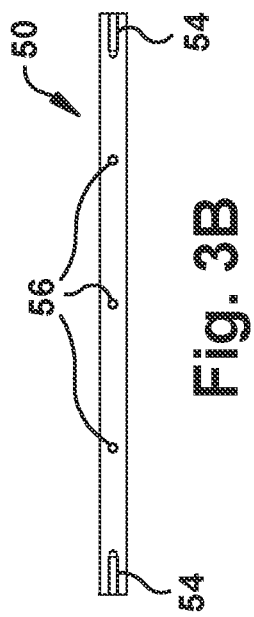
Figure 3A:
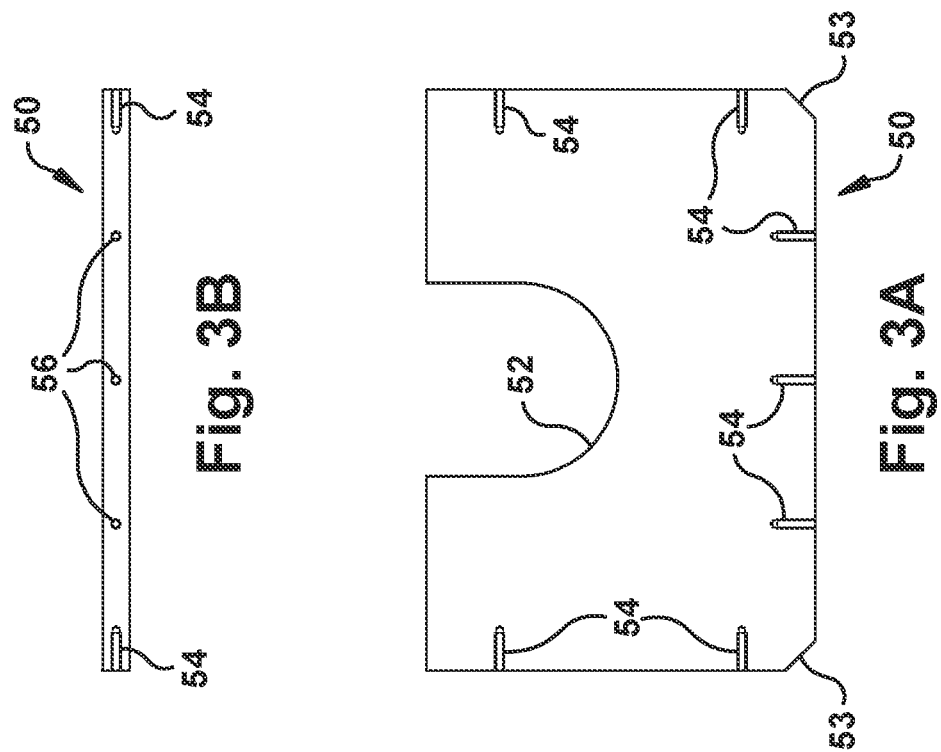

In one embodiment, a series of head screws 54 may be included on 3 sides of side plate 50. Screw holes 56 are provided at the end of side plate 50 as shown in FIG. 3B.

Figure 4B:
FIGS. 3 and 4 are schematic views of a side plate and a cross plate used as a housing for other components of present embodiment of the innovation.
Figure 4A:
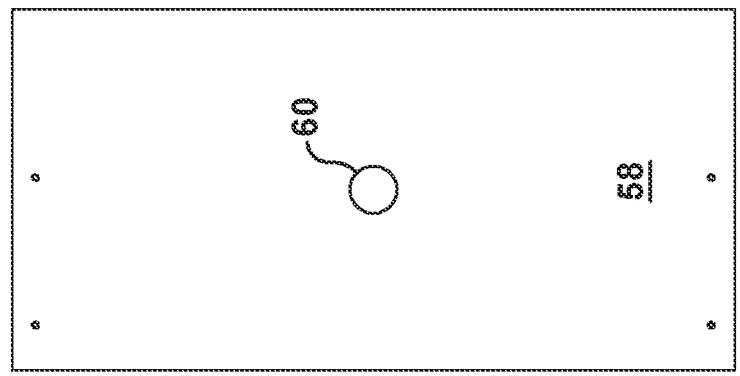

A cross plate 58 is shown in FIGS. 4A and 4B. FIG. 4A is a plan view of cross plate 58. Cross plate 58 includes an aperture 60.

Referring to FIGS. 5A-5D, a support frame 62 is shown for an embodiment according to the innovation. FIG. 5A is a plan view, FIG. 5C is an end view and FIGS. 5B and 5D are side views.

FIGS. 6A-6B depict an embodiment according to an aspect of the innovation and shows the cover for support frame 62. FIG. 6 shows a cover 64, with FIG. 6A being a plan view and FIG. 6B being an end view. FIG. 6A shows that cover 64 has a rectangular cross section with a U-shaped handle 66. Emergency respirator ventilator 10 is portable and can be carried by means of handle 66 when it is closes support frame 62.

Figure 7A:
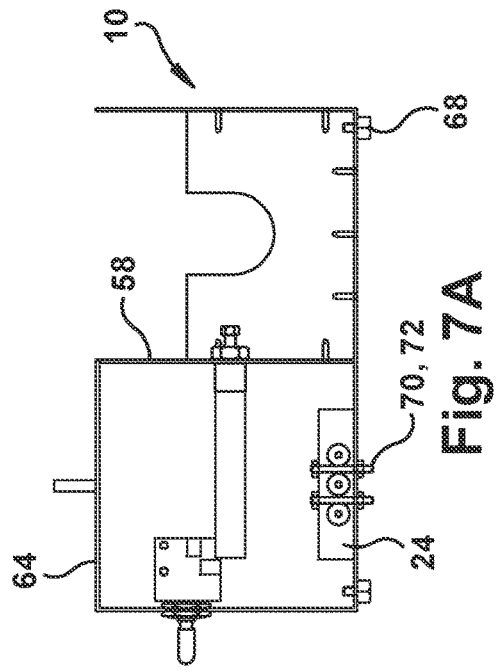
FIG. 7 is a schematic view of an overall assembly of a respirator ventilator according to an embodiment of the innovation.
Figure 7B:
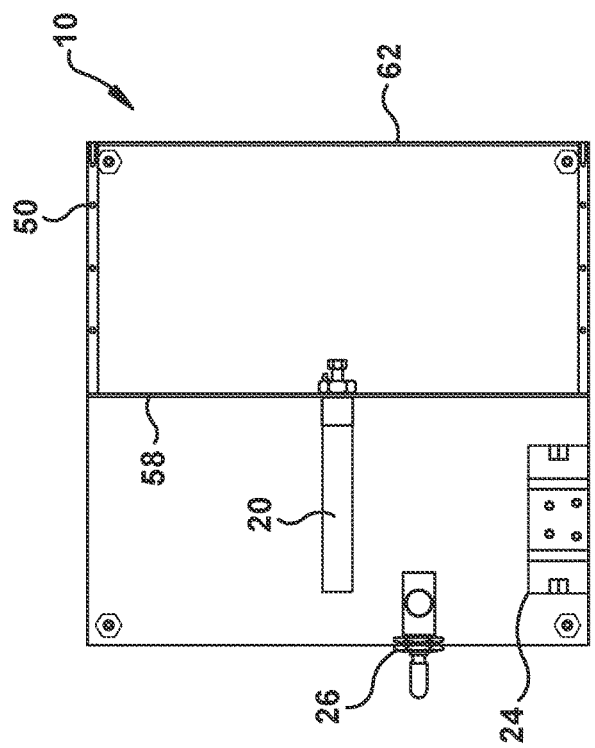
Figure 7C:
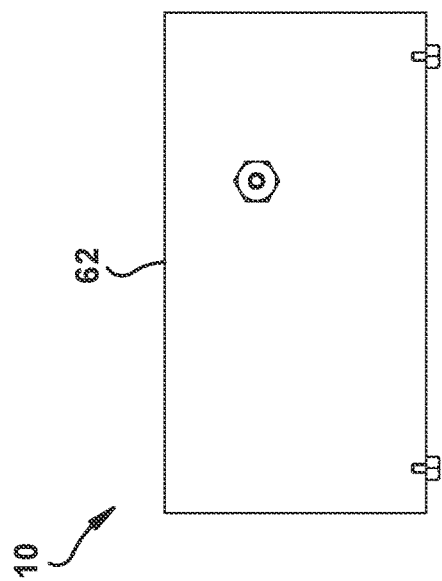

FIGS. 7A-7C depiction overall assembly for respirator ventilator 10 according to an embodiment. FIG. 7A is a side view of the emergency respirator ventilator 10. FIG. 7B is a plan view of respirator ventilator 10. FIG. 7C is a side view of respirator ventilator 10. Support frame 62 is shown in FIG. 7C. Side plate 50 is illustrated in FIG. 7B. FIG. 7A shows cross plate 58. Also shown in FIG. 7A is cover 64. A front and rear mount double ended air cylinder 20 (e.g., Bimba 3" stroke) is depicted in FIG. 7B. Also shown in FIG. 7B is a four way five port air pilot valve 24 and three way three port manual toggle 26. Threaded stud bumpers 68 may be further provided. A pair of stainless button head screws 70 and hex nuts 72 through screws 70 extend are shown in FIG. 7A.

Figure 8:
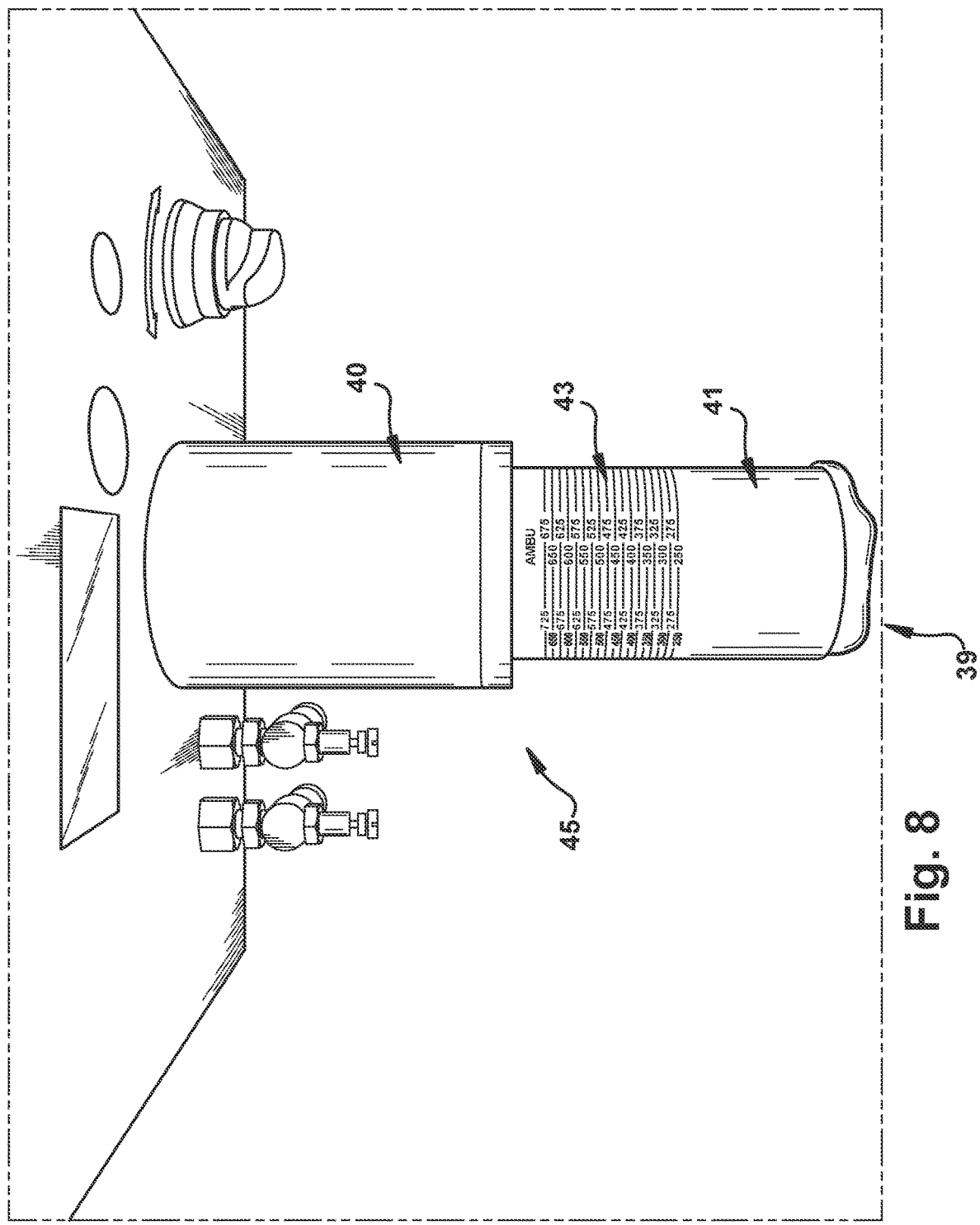
FIG. 8 is perspective photograph of a tube-in-tube calibration device according to an embodiment of the innovation.

According to an aspect, the respirator ventilator may provide an adjustable tidal volume to a patient. The tidal volume may be adjusted by, for example, adjusting the stroke of the piston/piston assembly. This in turn allows for a different rate of compression of the compressible air bag. Once selected, the respirator ventilator supplies a constant tidal volume to the patient by applying a consistent pressure to the compressible air bag. FIG. 8 depicts an embodiment of a "tube-in-tube" calibration device 45 for adjusting the stroke of piston rod 34. The calibration device 45 may include an outer cylinder/tube 40 and an inner cylinder/tube 41. The inner cylinder/tube 41 may be configured to slidably fit within the outer cylinder tube 40. The inner cylinder 41 may be a graduated, adjustable inner tube having markings corresponding to tidal volume 43. Locking cap 39 locks the adjustable inner tube 41 in place once the desired tidal volume is selected. It will be appreciated that other means for adjusting the stroke of the piston or for adjusting the tidal volume may be used. For example, magnetic sensors, stroke completion sensors and/or proximity sensors may be used. These embodiments are to be included within the scope of the innovation described as well as the claims appended hereto.

Figure 9:
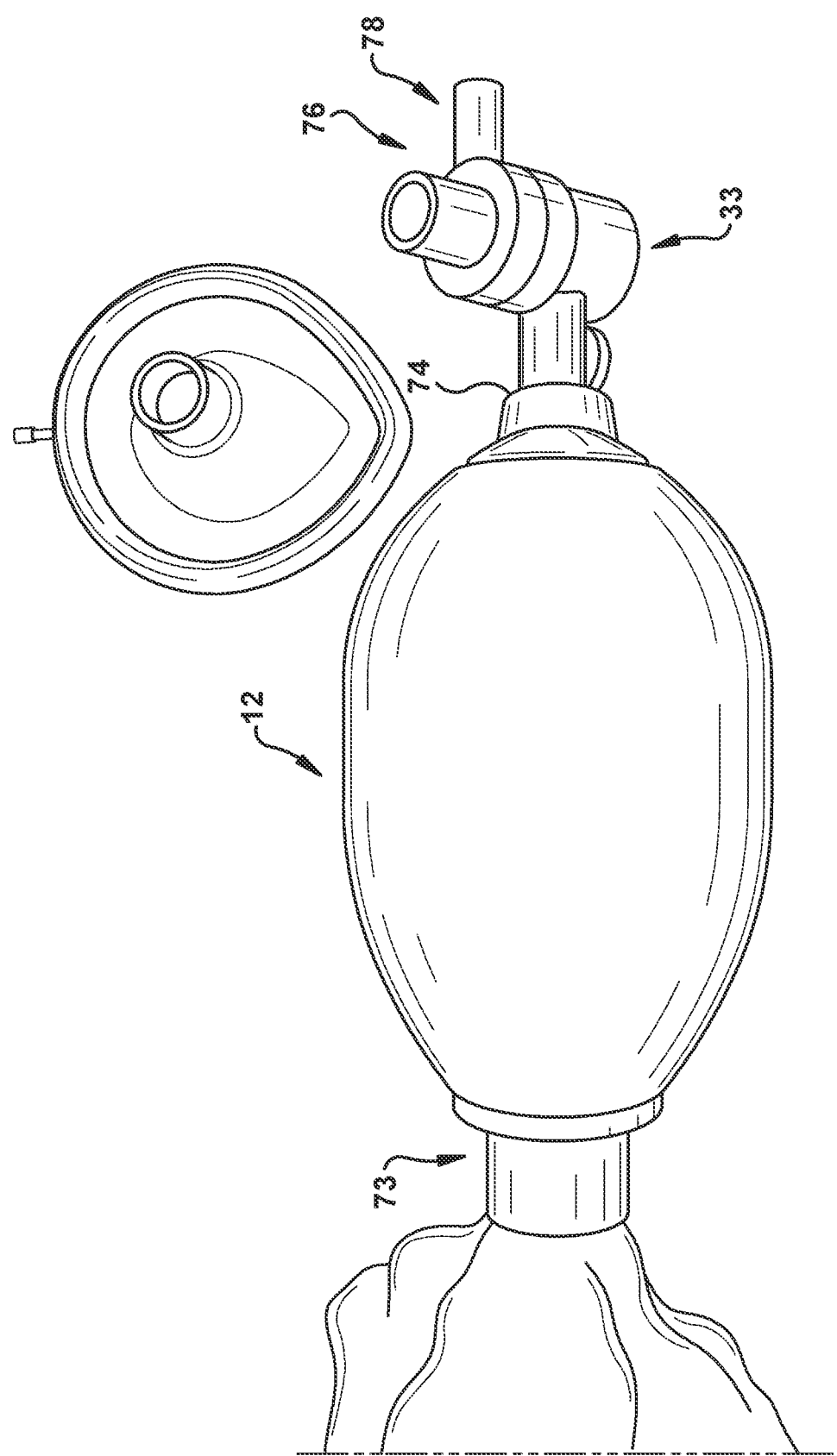
FIG. 9 is a perspective photograph of the air containing bag that may be incorporated into an embodiment according to the innovation.

Turning next to FIG. 9, self-inflating air bag 12 comprises an intake end with an inlet port 73, and outlet port 74 with a patient valve device 33 and tube 76 for providing an access to the patient's mouth to receive air, oxygen or a combination of air and oxygen as required. A tube 78 is also shown for receiving waste gas from the patient (not used in this resuscitator ventilator device).

Respirator ventilator 10 is very effective as an emergency device. In some embodiments, it only incorporates one moving part, namely integral piston rod 34-domed pressure plate 32 for squeezing self-inflating air bag 12 in order to provide oxygen to a patient. In one embodiment, the unit is very portable, weighing less than about twenty pounds (a unit according to an embodiment of the innovation may be about fifteen pounds). In one embodiment, the unit has approximately a 12"×12" footprint. In the aspect described above, it is operated by compressed air. Low voltage electric power provides current for the display, solenoids, and the alarms. It is to be appreciated that electrically powered units can be employed in a similar manner as those described supra with regard to pneumatic embodiments. These electrically-powered embodiments are to be included within the scope of the innovation described as well as the claims appended hereto. In operation, the unit can provide at least thirty-five breaths per minute, which is-higher than the standard requirement or performance metrics of conventional systems. Today, it is believed that this unit could be very affordable. Its cost is based on the purchase price and the operating costs would be much less expensive than not only multi-modal ventilators, but also simpler ventilators presently available. Currently used ventilators have operating costs higher than those according to an embodiment of the innovation because the currently available "low cost" gas driven ventilators use high volumes of more expensive medical grade oxygen.

As indicated above, in some embodiments an alarm system may be included. An alarm may be activated when a BVM bag breaks, when the BVM bag is disconnected, when high pressure occurs (such as in the event that the patient is unconscious or sedated), in the event a tube is blocked or a tube is kinked, and when the patient's lungs become inelastic and it is necessary to maintain a-higher pressure. According to an aspect, an embodiment of the innovation may include an appropriate alarm system.

In one embodiment, the unit may include a display unit. The display unit may display PIP, PEEP, Respiration Rate, I/E ratio, Inspiration Time, and alarms, measurements of appropriate pressure readings, improper tube connections etc. In one embodiment, the display may include an alarm reset button. In one embodiment, the reset button is manually operated.

Figure 10:
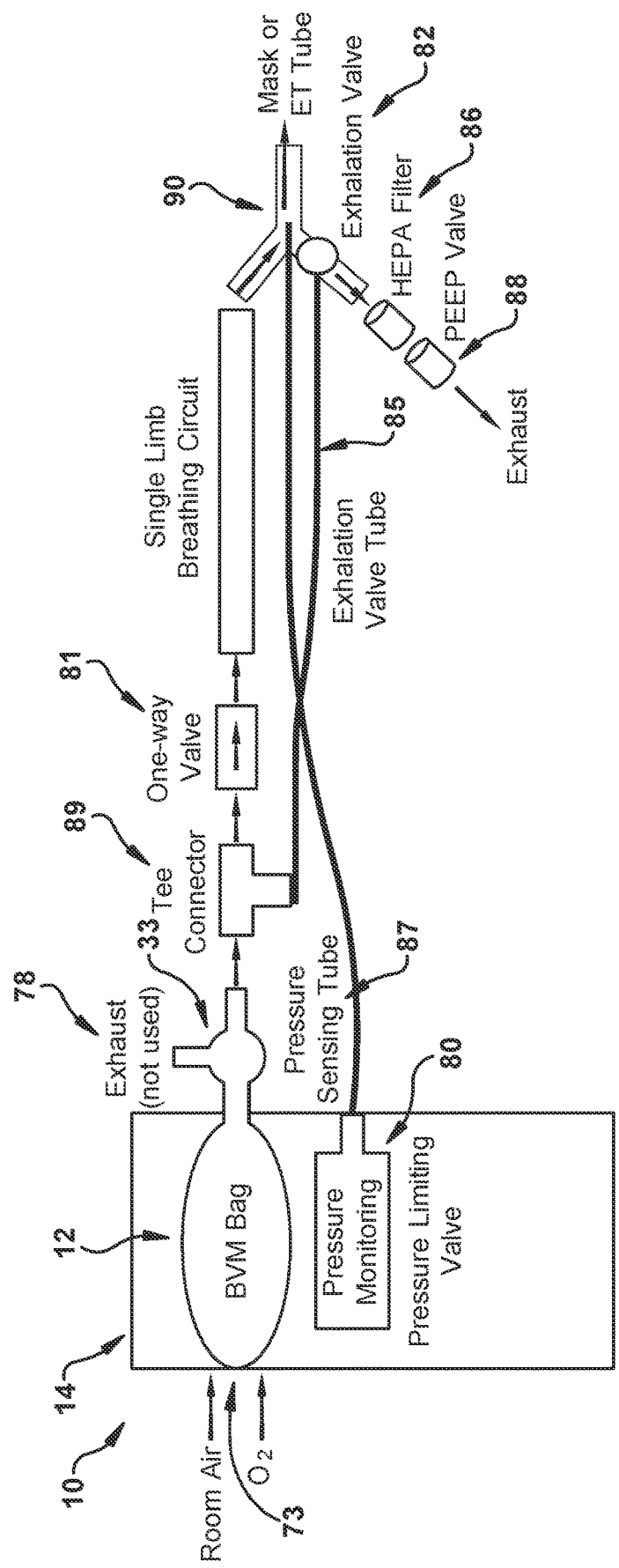
FIG. 10 is a schematic view of a respiratory ventilator system according to an embodiment of the innovation.

Referring to FIG. 10, a pressure monitoring sensor 80 is disposed in the cylinder chamber. A tube 87 connects the sensor module to a pressure port in the patient circuit near the patient's mouth. An exhalation/exhaust valve 82 including an exhalation valve tube 85 leading thereto is operatively connected to a tee 89 that feeds pressure through a small tube 85 to the exhaust valve 82. This provides simple and reliable control to close the exhalation valve during inhalation ensuring the prescribed tidal volume of air is delivered to the patient. Once compression of the compressible air bag 12 is complete, the pressure provided by this configuration ceases, allowing for exhalation. Also attached to the tee 89 is a disposable one-way flapper valve 81 for blocking the exhaust from exiting the patient valve tube 78 to enable PEEP. This allows the use of multiple configurations of BVMs that may have different exhaust port systems. One-way flapper valve 81 is connected by the single limb breathing circuit to a wye 90 at the patient. The exhaust tube from the wye is connected to the exhaust valve 82, the adjustable PEEP valve 88 and the HEPA filter 86 where exhaust exits to the room. This configuration provides the ability to adjust air supply (e.g., respiration rate, tidal volume, and I/E ratio) for a patient through the control of the air cylinder 20 via adjustment of the flow control valves 22 and the tube in tube assembly 45.

Figure 11:
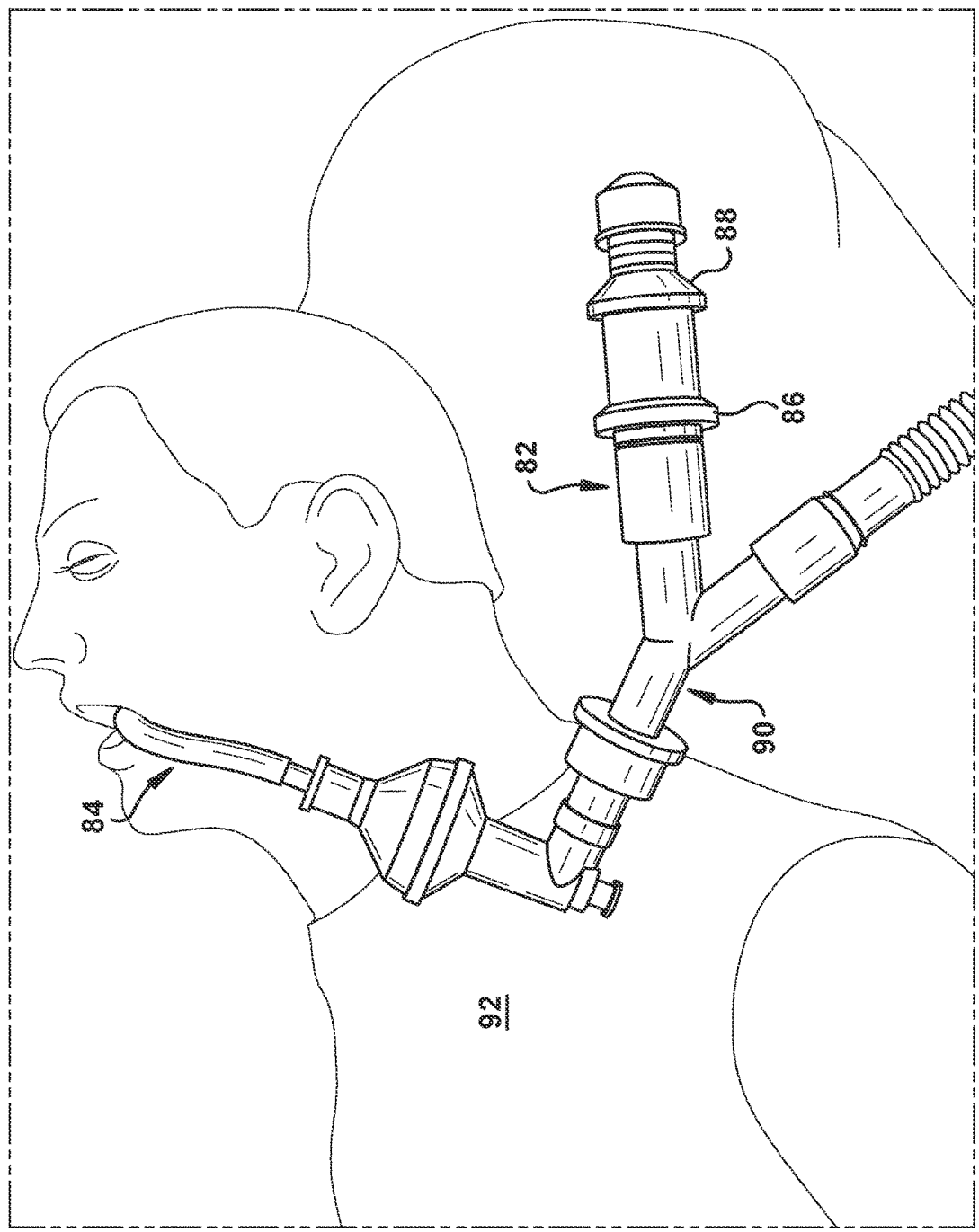
FIG. 11 is a photograph of a manikin having a tubular assembly aspect to a portion according to an embodiment of the innovation inserted in the mouth of the manikin.

Turning to FIG. 11, a manikin 92 in the form of a human is shown having air inlet tube 84 being received in the mouth of manikin 92.

The innovation has been described in detail, and those familiar with the art will be able to understand the relevant elements of the device disclosed herein, with reference to the description set forth above and from the appended claims.

What is claimed is:

1. A pneumatically controlled respirator ventilator system comprising:
 a housing configured to accommodate a compressible air bag operatively connected to a supply of air, oxygen, or a combination of air and oxygen;

a pneumatic piston assembly comprising:
an air cylinder,
a pneumatically controlled piston apparatus comprising a piston rod,
an air bag compression surface configured to compress the compressible air bag during an inhalation cycle;
a piston rod stroke controller comprising a tube-in-tube combination comprising:
a hollow outer tube,
a threaded inner tube extending within the outer tube, wherein the threaded inner tube is configured to rotate to vary the stroke of the piston rod and wherein, the threaded inner tube comprises a portion of the piston rod,
a selectable calibration scale comprising markings on the hollow outer tube or the threaded inner tube corresponding to a tidal volume, and
a locking knob configured to secure the position of the inner tube;
a tubular gas transmission assembly for transmitting an adjustable supply of air, oxygen, or a combination of air and oxygen to a patient in response to compression of the compressible air bag, and
an exhaust valve configured to close due to pressure caused by compression of the compressible air bag and to open when the compressible air bag is not being compressed.

2. The pneumatically controlled respirator ventilator system of claim 1, wherein the pneumatically controlled piston apparatus is an electro-pneumatically controlled piston apparatus.

3. The pneumatically controlled respirator ventilator of claim 1, wherein the air cylinder is a double ended air cylinder and the air bag compression surface is a domed compression plate, where the front and rear mount double ended cylinder is operationally attached to the domed compression plate.

4. The pneumatically controlled respirator ventilator system of claim 1, further comprising:
a tee connector, and
an exhalation valve tube connecting the tee connector and the exhaust valve,
wherein pressure associated with compression of the compressible air bag is transmitted via exhalation valve tube to the exhaust valve.

5. The pneumatically controlled respirator ventilator system of claim 1, wherein the housing comprises:
a compression compartment for containing the compressible air bag and the air bag compression surface;
an air cylinder compartment for containing the air cylinder, and the pneumatically controlled piston apparatus; and
a wall between the compression compartment and the air cylinder compartment, the wall defining an opening for enabling the pneumatically controlled piston apparatus to move towards the compressible air bag to cause the air bag compression surface to compress the air bag to cause air, oxygen, or a combination of air and oxygen from within the compressible air bag through the tubular gas transmission assembly to a patient.

6. The pneumatically controlled respirator ventilator system of claim 5, wherein the compression compartment further includes a receiving plate configured to accommodate the compressible air bag so as to reduce erratic movement of the compressible air bag during compression.

7. The pneumatically controlled respirator ventilator system of claim 1, further comprising a display operatively connected to the pneumatically controlled respirator ventilator system for displaying at least one of a respiration rate, an I/E ratio, a positive end-expiratory pressure (PEEP), inspiration time, and peak inspiration pressure.

8. The pneumatically controlled respirator ventilator system of claim 1, wherein the pneumatically controlled piston apparatus further comprises a stroke completion sensor or valve.

9. The pneumatically controlled respirator ventilator system of claim 1, wherein the tubular gas transmission assembly comprising:
an inhalation breathing circuit comprising a one way flapper valve; and
an exhaust breathing circuit comprising the exhaust valve, wherein gases from the exhaust breathing circuit are prevented from flowing into the inhalation breathing circuit by the flapper valve.

10. A pneumatically controlled respirator ventilator for effecting an inhalation cycle of a patient, the pneumatically controlled respirator ventilator comprising:
a piston-cylinder assembly comprising a double ended air cylinder and a pneumatic drive piston;
a piston rod stroke controller comprising a tube-in-tube combination comprising:
a hollow outer tube,
a threaded inner tube extending within the outer tube, wherein the threaded inner tube is configured to rotate to vary the stroke of the pneumatic drive piston and wherein, the threaded inner tube comprises a portion of the pneumatic drive piston,
a selectable calibration scale comprising markings on the hollow outer tube or the threaded inner tube corresponding to a tidal volume, and
a locking knob configured to secure the position of the inner tube;
an air bag compression surface operatively connected to the pneumatic drive piston, wherein the air bag compression surface is configured to compress a compressible air bag operatively connected to a supply of air, oxygen, or a combination of air and oxygen, during an inhalation cycle; and
an exhaust valve configured to close due to pressure caused by compression of the compressible air bag and to open when the compressible air bag is not being compressed, wherein the piston-cylinder assembly is configured to move the pneumatic drive piston in a reciprocating motion so as to compress the compressible air bag by engaging the air bag compression surface.

11. The pneumatically controlled respirator ventilator of claim 10, wherein the air bag compression surface is a dome-shaped portion of the pneumatic drive piston.

12. The pneumatically controlled respirator ventilator of claim 10, where the pneumatic drive piston is an electro-pneumatically controlled piston.

13. The pneumatically controlled respirator ventilator of claim 10 further comprising a housing, wherein the housing comprises:
a compression compartment for containing the compressible air bag;
a piston-cylinder compartment for containing the piston-cylinder assembly and the pneumatic drive piston; and
a wall between the compression compartment and the piston-cylinder compartment, the wall defining an opening for enabling the pneumatic drive piston to move towards the compressible air bag to cause the air bag compression surface to compress the air bag to cause air, oxygen, or a combination of air and oxygen from within the compressible air bag through an inhalation circuit of a tubular assembly to a patient, the tubular assembly comprising a inhalation circuit comprising a tee connector, a one way flapper valve, a wye, a patient connection, and an exhaust circuit.

14. The pneumatically controlled respirator ventilator of claim 13, wherein the exhaust circuit of the tubular assembly further comprises:
   an exhalation valve, and
   an exhalation valve tube connecting the tee connector and the exhaust valve,
wherein pressure associated with compression of the compressible air bag is transmitted via exhalation valve tube to the exhaust valve.

15. The pneumatically controlled respirator ventilator of claim 10, wherein the pneumatic drive piston is a variable stroke piston having an adjustable effective length.

\* \* \* \* \*